US008834169B2

(12) United States Patent
Reinkensmeyer et al.

(10) Patent No.: US 8,834,169 B2
(45) Date of Patent: Sep. 16, 2014

(54) METHOD AND APPARATUS FOR AUTOMATING ARM AND GRASPING MOVEMENT TRAINING FOR REHABILITATION OF PATIENTS WITH MOTOR IMPAIRMENT

(75) Inventors: David Reinkensmeyer, Irvine, CA (US); Robert J. Sanchez, Jr., Oceanside, CA (US); Punit Shah, La Mirada, CA (US); Robert F. Smith, Jr., Costa Mesa, CA (US)

(73) Assignee: The Regents of the University of California, Oakland, CA (US)

( * ) Notice: Subject to any disclaimer, the term of this patent is extended or adjusted under 35 U.S.C. 154(b) by 1911 days.

(21) Appl. No.: 11/512,670

(22) Filed: Aug. 30, 2006

(65) Prior Publication Data
US 2007/0060445 A1    Mar. 15, 2007

Related U.S. Application Data

(60) Provisional application No. 60/713,575, filed on Aug. 31, 2005.

(51) Int. Cl.
| G09B 9/00 | (2006.01) |
| A61H 1/02 | (2006.01) |
| A61B 5/11 | (2006.01) |
| A61B 5/00 | (2006.01) |
| B25J 9/00 | (2006.01) |
| A61F 5/01 | (2006.01) |

(52) U.S. Cl.
CPC ............ *A61H 1/0274* (2013.01); *A61H 1/0237* (2013.01); *A61H 1/0281* (2013.01); *A61B 5/1116* (2013.01); *A61H 2201/5064* (2013.01); *A61B 5/486* (2013.01); *A61B 5/1124* (2013.01); *A61B 5/4528* (2013.01); *A61B 5/11* (2013.01); *B25J 9/0006* (2013.01); *A61F 5/0102* (2013.01); *A61B 5/4519* (2013.01); *A61H 2201/5007* (2013.01)
USPC ................ 434/247; D24/188; 601/5; 601/33; 482/8; 600/587

(58) Field of Classification Search
CPC ........ A61B 5/4528; A61B 5/11; A61B 5/486; A61B 5/1116; A61B 5/4519; A61B 5/1124; A61H 1/0274; A61H 1/0237; A61H 1/0281; A61H 2201/5064; B25J 9/0006; A61F 5/0102
USPC ............ 434/247; D24/188; 601/5, 33; 482/8; 600/587
See application file for complete search history.

(56) References Cited

U.S. PATENT DOCUMENTS

| 4,651,719 A | 3/1987 | Funk et al. |
| 4,975,016 A | 12/1990 | Pellenc et al. |

(Continued)

FOREIGN PATENT DOCUMENTS

NL    1009886    8/1998

OTHER PUBLICATIONS

A Pneumatic Robot for Re-Training Arm Movement After Stroke: Rationale and Mechanical Design, R. J. Sanchez, Jr. et al., Proceedings of the 2005 IEEE, 9th International Conference on Rehabilitation Robotics, Jun. 28-Jul. 1, 2005,Chicago, IL, pp. 500-504—(Enclosed).

*Primary Examiner* — Jack Yip
(74) *Attorney, Agent, or Firm* — Marcus C. Dawes; Daniel L. Dawes

(57) ABSTRACT

A method and apparatus for upper limb rehabilitation training of coordinated arm/forearm, forearm/forearm and grasping movements of a motor impaired patient comprises a nonrobotic, passive support, an arm/forearm sensor, a gripping device, a grip sensor capable of measuring an impaired grasping force of a grasping of the patient, a computer to process measurements of coordinated and simultaneous impaired arm/forearm, forearm/forearm and grasping movements to control a graphical representation of the arm/forearm and grasping movements in interaction with a virtual environment, and to provide a visual feedback signal to the patient of simulated normal activities of daily living performed with enhanced motor ability relative to the actual impaired motor ability. A visual feedback signal of the simulated activities of daily living is provided to motivate the patient to perform the upper limb rehabilitation movement training despite limited motor ability.

32 Claims, 5 Drawing Sheets

(56) References Cited

U.S. PATENT DOCUMENTS

| | | | |
|---|---|---|---|
| 5,231,998 A | 8/1993 | Rosen et al. | |
| 5,417,643 A | 5/1995 | Taylor | |
| 5,429,140 A | 7/1995 | Burdea et al. | |
| 5,466,213 A | 11/1995 | Hogan et al. | |
| 5,800,561 A | 9/1998 | Rodriguez | |
| 5,954,621 A * | 9/1999 | Joutras et al. | 482/114 |
| 6,007,500 A * | 12/1999 | Quintinskie, Jr. | 601/5 |
| 6,155,993 A * | 12/2000 | Scott | 600/595 |
| 6,613,000 B1 | 9/2003 | Reinkensmeyer et al. | |
| 6,821,259 B2 | 11/2004 | Rahman et al. | |
| 6,827,579 B2 | 12/2004 | Burdea et al. | |
| 6,872,187 B1 * | 3/2005 | Stark et al. | 602/16 |
| 6,918,862 B1 * | 7/2005 | Comeau | 482/111 |
| 7,416,537 B1 * | 8/2008 | Stark et al. | 602/16 |
| 7,547,289 B2 * | 6/2009 | Branch | 601/5 |
| 2002/0082530 A1 * | 6/2002 | Knoll | 601/23 |
| 2003/0054923 A1 * | 3/2003 | Brassil et al. | 482/49 |
| 2003/0115954 A1 * | 6/2003 | Zemlyakov et al. | 73/379.01 |
| 2003/0120183 A1 * | 6/2003 | Simmons | 600/595 |
| 2004/0067832 A1 * | 4/2004 | Hassler | 482/142 |
| 2004/0153010 A1 * | 8/2004 | Bonutti et al. | 601/5 |
| 2004/0267331 A1 * | 12/2004 | Koeneman et al. | 607/49 |
| 2005/0130815 A1 * | 6/2005 | Abdoli-Eramaki | 482/121 |
| 2006/0150753 A1 * | 7/2006 | Massimo et al. | 73/865.4 |
| 2006/0293617 A1 * | 12/2006 | Einav et al. | 601/33 |

\* cited by examiner

METHOD AND APPARATUS FOR AUTOMATING ARM AND GRASPING MOVEMENT TRAINING FOR REHABILITATION OF PATIENTS WITH MOTOR IMPAIRMENT

RELATED APPLICATIONS

The present application is related to U.S. Provisional Patent Application, Ser. No. 60/713,575, filed on Aug. 31, 2005, which is incorporated herein by reference and to which priority is claimed pursuant to 35 USC 119.

STATEMENT OF GOVERNMENT SUPPORT

This invention was made with Government support under grant RR000827 awarded by the National Institute of Health, and grant H133E020724 awarded by the US Department of Education. The Government has certain rights in this invention.

BACKGROUND OF THE INVENTION

1. Field of the Invention

The invention relates to the field of rehabilitation methods and apparatus for retraining of patients with motor impairment such as stroke, spinal cord injury, traumatic brain injury, cerebral palsy, multiple sclerosis, peripheral nerve injury or the like.

2. Description of the Prior Art

Each year in the U.S. over 700,000 people survive a stroke. Approximately 50% of stroke survivors have chronic hemiparesis. Movement impairments are typically treated with intensive, hands-on physical and occupational therapy for several weeks after the initial injury. Unfortunately, due to economic pressures on the U.S. health care system, stroke patients are receiving less therapy than before. Consequently, the home rehabilitation that results from these pressures is self directed with little professional or quantitative feedback. Approximately 26% of chronic stroke survivors become dependent in activities of daily living. A growing body of evidence suggests that both acute and chronic stroke survivors can improve movement ability with intensive, supervised training.

When people suffer a severe stroke or other serious neural injury, they often have difficulty lifting the arm against gravity, and opening and closing the hand. Their inability to move the upper limb in a useful way is very frustrating, and they stop trying to move the limb, leading eventually to a further decreased ability to use the limb because of the physiological changes in muscle and neural tissue associated with prolonged disuse. Rehabilitation therapists and other caregivers encourage their patients to practice moving in order to regain some function, but one-on-one, hands-on interaction with a professional caregiver is expensive. People often do not continue to practice moving once they leave the hospital environment.

Several researchers are addressing this goal by developing robotic devices that can assist in arm and hand movement therapy following stroke. Initial studies with MIT-MANUS (see U.S. Pat. No. 5,466,213), MIME, the ARM Guide, Gentle-S and Rutgers Master II-ND have been promising. Acute and chronic stroke subjects who receive more therapy with a robotic device can recover more movement ability. Matched amounts of robotic and conventional therapy produced comparable therapeutic benefits for chronic stroke subjects.

Despite these promising initial results, it still remains unclear as to whether the robotic features of these devices (i.e. the ability to apply programmable forces to the patient's limb), are important to improving movement recovery. That is, technology that allows patients to practice movement therapy without robotic actuation may also be effective in improving recovery. While non-robotic devices are less useful for studying a broad range of interactive therapy techniques, they might ultimately be more practical because they avoid the expense and safety concerns associated with robotic actuators.

There is a long history of using non-robotic technology in rehabilitation clinics to partially automate physical rehabilitation following stroke. Mobile arm supports, overhead slings, elastic bands, and weights allow patients to practice therapy semi-independently from therapists. However, these devices typically suffer from three key limitations: they can be difficult to adjust for different levels of impairment; their relevance to functional activities is indirect; and they provide little feedback to the patient or therapist about movement recovery.

What is needed is an apparatus and method that allows the rapidly growing stroke population to practice intensive movement training without the expense of a continuously present therapist.

BRIEF SUMMARY OF THE INVENTION

The illustrated embodiment of the invention is directed to a low-cost, passive orthosis for arm movement training after stroke. The disclosure describes the rationale and initial development of the orthosis for movement training.

The illustrated embodiment provides a means for people with severe weakness of the upper limb to practice moving their arm in a meaningful, motivating, effective way. The illustrated embodiment of the invention is comprised of a mobile arm support that uses rubber bands to relieve the weight of the arm. It also is comprised of sensors that detect the motion of the arm and the grasping force of the hand. It must be understood that while in the illustrated embodiment the hand gripper includes a fluidic bladder for measuring the force of grasping, it is also expressly contemplated that the extent of grasping movement could be equivalently measured and used, not only in an average sense, but also as could be mechanically measured for different fingers or parts of the hand.

A computer program reads in these measurements, then uses the measurements to control a graphical representation of the arm and hand. The user interacts with a virtual environment in order to practice simulated activities of daily living such as reaching for items on a shelf, eating, or cooking. Even very weak people can perform these simulated activities because they don't have to overcome gravity to lift their arm, and they only need to be ability to grip very lightly to activate the grasp sensor. Further, the level of difficulty of the system can be easily changed to match the level of ability of the user by adding or removing rubber bands to the arm support, and by adjusting the software to raise or lower the grasp force threshold required to "grab" virtual objects, or to change the amount of movement of the arm required to achieve the simulated activities of daily living The combined action of providing support for the arm, measuring even small amounts of hand grasp, and simulating activities of daily living with computer software is much more effective than the individual elements alone, because the arm and the hand are typically used together for most activities, and because people are highly motivated to practice motor activities that help them with their daily life.

The robot utilizes the Wilmington Robotic Exoskeleton (WREX) (see U.S. Pat. No. 6,821,259 incorporated herein by reference), which includes a passive, mobile arm support developed for children with arm weakness caused by a debilitative condition. We have modified the commercially available device so that it is scaled for use by adults, instrumented it with potentiometers, and incorporated a grip strength sensor. The resulting passive device, which we call the Therapy WREX or "T-WREX", allows individuals with severe motor impairment to practice functional movements, such as reaching, eating, and washing, in a virtual reality environment called Java Therapy 2.0.

Thus, it is to be understood that the illustrated embodiments encompass an apparatus for upper limb rehabilitation training of coordinated arm, forearm and grasping movements of a patient comprising a nonrobotic, passive arm/forearm support to support and facilitate movement of the arm and forearm of the patient, an arm/forearm sensor capable of measuring impaired arm and forearm movements of the arm and forearm of the patient, a gripping device for grasping by the patient, a grip sensor capable of measuring an impaired grasping force of a hand of the patient, a computer coupled to the arm/forearm sensor and the grip sensor to process measurements of coordinated and simultaneous impaired arm, forearm and grasping movements to control a graphical representation of the arm and hand movements in interaction with a virtual environment, and to provide a visual feedback signal to the patient of simulated normal activities of daily living performed with enhanced motor ability relative to the actual impaired motor ability, and a display device coupled to the computer to display the visual feedback signal of the simulated activities of daily living. As a result motivation is provided to the patient to perform the upper limb rehabilitation movement training despite limited motor ability.

In one embodiment the nonrobotic, passive arm/forearm support comprises an adjustment mechanism or means to vary a force level required to move the arm, forearm or apply the grasping force and/or a movement range of the arm, forearm or the grasping force required to successfully perform the simulated activities of daily living. The computer comprises an adjustment means or software to vary a threshold level for detecting the grasping force and a releasing movement.

The nonrobotic, passive arm support comprises an elastic suspension and a five degrees-of-freedom exoskeleton which counterbalances the weight of the arm using the elastic suspension. More specifically, the nonrobotic, passive arm support comprises a five degrees-of-freedom, back-drivable exoskeleton using elastic bands wrapped around two four bar linkages to counterbalance the arm. The nonrobotic, passive arm support facilitates forearm supination and pronation, elbow flexion and extension, in combination with shoulder internal and external rotation, flexion and extension, and abduction and adduction.

The nonrobotic, passive arm support comprises means for reaching, drawing, eating, cooking, and cleaning or personal hygiene movements. The arm/forearm sensor has a measurement resolution of the distal tip of the nonrobotic, passive arm support within 1 cm for each of the plurality of movement axes. The arm/forearm sensor measures impaired arm movements and impaired grasping force and releasing movements without initial zeroing, so that no initialization procedures are required. In the illustrated embodiment the grip sensor comprises a fluidic bladder and a pressure sensor coupled to the bladder.

In one embodiment a remote computer network coupled to the computer from which network the computer is controlled to provide the visual feedback signal in a plurality of user-selected simulated activities of daily living.

The computer generates quantitative feedback of performance, and/or rehabilitative therapy and therapeutic history of performance.

The invention also includes within its scope a computerized method for training arm, forearm and/or hand grasping movements of a patient using any one of the foregoing apparatus. The illustrated method comprises the steps of facilitating movement of an arm and/or forearm of the patient with a nonrobotic, passive arm support; measuring impaired arm and/or forearm movements of an arm and/or forearm of the patient; measuring impaired grasping forces of a hand of the patient; and generating a visual feedback to the patient of simulated normal activities of daily living in a virtual environment performed with enhanced motor ability relative to the actual impaired motor ability by use of a computer having arm/forearm measurement and grasping measurements as simultaneous, coordinated inputs.

The computer is controlled to provide the visual feedback signal in a plurality of user-selected simulated activities of daily living comprises controlling the computer to provide the visual feedback signal for shopping, washing an object, food handling, performing acts of personal hygiene, eating and/or ranging the arm.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

BRIEF DESCRIPTION OF THE DRAWINGS

FIG. 2a is a layout diagram of a peg pattern on a board and FIG. 2b is a perspective view of the peg board of FIG. 2a.

FIG. 3a illustrated an impaired arm and FIG. 3b an unimpaired arm.

FIG. 4a is a graph of the average reaching range of motion across subjects to targets with and without gravity balance (distance traveled to target/total distance to target). (*paired t-test, p<0.05). FIG. 4b is the average height reached above lap, with and without gravity balance. (*paired t-test, p<0.05). FIG. 4c is an example data from one subject as she attempted to trace a circle 30 times, without gravity balance (top four panels) and with gravity balance (bottom four panels).

FIG. 5a is the mean percent range of motion across four subjects and three trials. Percent range of motion was calculated by subtracting the mean distance traveled on the first day from the daily movements, then dividing the difference by the mean distance between the start point and target. FIG. 5b is an ensemble average of normalized game scores (possible range 0 to 1) for three games (Shopping, Ranging the Arm, and Cleaning the Stove) across the four subjects who completed all eight weeks of movement training.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

An important goal in rehabilitation engineering is to develop technology that allows individuals with severe motor impairment to practice arm movement without continuous supervision from a rehabilitation therapist. A first embodiment is illustrated by a system, called Therapy WREX or ("T-WREX") 10. The system 10 is comprised of an orthosis that assists in arm movement across a large workspace, a grip sensor 20 that detects hand grip pressure, and software controlled computer 14 that simulates functional activities. The arm orthosis is an instrumented, adult-sized version of the Wilmington Robotic Exoskeleton (WREX), which is a five degrees-of-freedom mechanism that counterbalances the weight of the arm using elastic bands.

After providing a detailed design description of T-WREX 10, this disclosure describes two pilot studies of the system's capabilities. The first study demonstrated that chronic stroke subjects whose arm function is compromised in a normal gravity environment can perform reaching and drawing movements while using T-WREX 10. The second study demonstrated that exercising the affected arm of five chronic stroke subjects with T-WREX 10 over an eight week period improved unassisted movement ability (mean change in Fugl-Meyer score was 5 points ±2 SD; mean change in range of motion of reaching was 10%, $p<0.001$). These results demonstrate the feasibility of automating upper-extremity rehabilitation therapy for severely impaired stroke patients using passive gravity assistance, a grip sensor, and virtual reality software.

Figure 1:
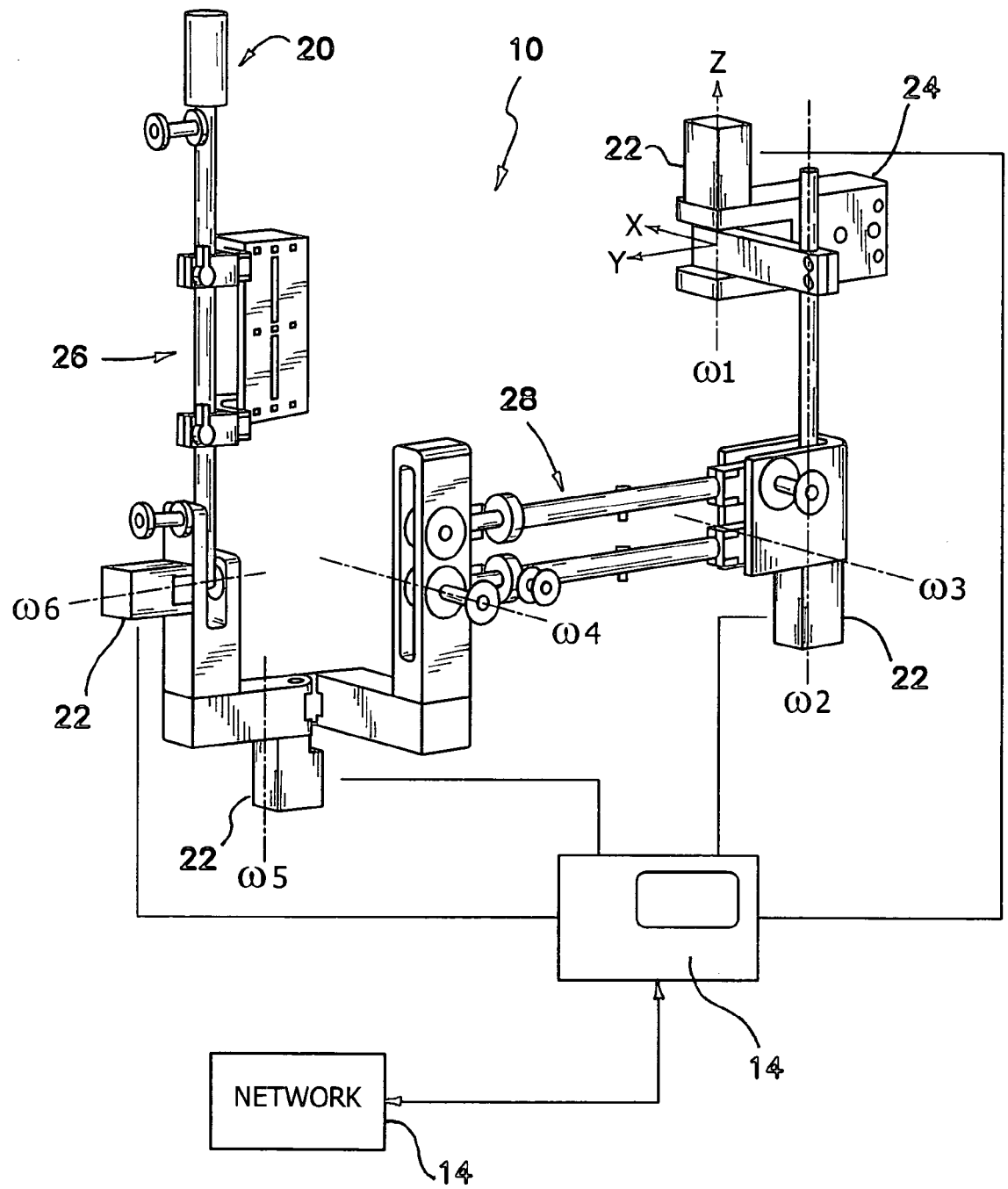
FIG. 1 is a diagram of the modified T-WREX with labeled axes of rotation with the gripper omitted.

This disclosure describes the development of a non-robotic system for upper extremity movement training that addresses these limitations as shown in the perspective view of TWREX 10 in FIG. 1. The system extends previously published work on a low-cost, highly accessible, web-based system for facilitating repetitive movement training, called "Java Therapy". The initial version of Java Therapy allowed users to log into a Web site, perform a customized program of therapeutic activities using a mouse or joystick, and receive quantitative feedback of their rehabilitation progress. In preliminary studies of the system, we found that stroke subjects responded enthusiastically to the quantitative feedback provided by the system. However, the use of a standard mouse or joystick as the input device limited the functional relevance of the system.

What was needed was an input device and software that allowed a broader range of functional arm movements to be practiced and monitored. We modified a conventional passive anti-gravity arm orthosis, the Wilmington Robotic Exoskeleton (WREX), to be used as a three dimensional input system 10 for measuring arm movement. We also developed a grip sensor 20 and software controlled computer 14 that allows the system to be used to practice simulated functional movements that require coordinated arm and hand movement.

This disclosure first provides a detailed design description of the arm orthosis coupled with the revised Java Therapy software. We then characterize the ability of the counterbalancing function of the arm orthosis to improve arm movement ability of stroke subjects while wearing the system 10. Finally, we report the results of a pilot study in which five chronic stroke subjects exercised their affected arm for two months using the system.

Methodology

WREX

WREX was originally designed to help children with weakened arms to perform activities of daily living such as eating. WREX is a five degrees-of-freedom, backdriveable mechanism that uses elastic bands wrapped around two four bar linkages to counterbalance the arm. WREX allows naturalistic movements across an estimated 66% of the normal workspace of the arm in the vertical plane and 72% in the horizontal plane.

We have modified WREX for use in movement training by stroke patients by making it larger, stronger, simpler to manufacture, and by instrumenting it with position sensors 22. We call the modified device, along with the enhanced version of software with which it is used, the T-WREX (Training WREX) system 10 as shown in FIG. 1.

T-WREX Design

Position Sensor Selection:

We desired a sensing system that allowed measurement resolution of the tip of T-WREX within 1 cm for all axes, which corresponds to a required angular resolution at the orthosis joints of about 0.3 degree. In addition, we desired a sensor 22 that did not require zeroing, so that users of the system 10 would not be required to execute any initialization procedures in order for the device to accurately measure movement. Conductive plastic, compact rotary potentiometers (Midori America, CP-2FB(b)) met these requirements and were installed in protective aluminum housings at each non-redundant joint indicated by the axes of rotation $\omega_i$ in FIG. 1.

Mechanical Design:

The primary design changes that we made to the conventional WREX design were to increase the size of the forearm link 26 and upper arm link 28 to accommodate an adult's arm. The user's arm is now attached to the device using a commercial brace (Elbow Ranger, edj-Orthopedics), which has lower and upper arm cuffs that attach with Velcro. The modified design can be flipped for use with the left or right arm by disassembling the device's elbow and forearm. The orthosis is attached at its shoulder 24 to an extruded-aluminum stand that is mounted to a manual wheelchair (not shown). The left-right, up-down, and forward-backward position of the orthosis can be quickly adjusted then locked into place using hand cranks.

Forward Kinematics:

In order to use the modified T-WREX 10 as a three dimensional mouse for the computer 14, it was necessary to define the forward kinematic relationship between the measured joint angles as depicted in FIG. 8 and the user's hand position. We used the product of exponentials formation for the forward kinematics. The position of the tip of the forearm link $p_t$ relative to a fixed reference frame located at the shoulder 24 is (FIG. 1):

$$p_t = e^{\xi_1\theta_1}e^{\xi_2\theta_2}e^{\xi_3\theta_3}e^{\xi_4\theta_4}e^{\xi_5\theta_5}e^{\xi_6\theta_6}M,$$

where the joint twists are:

$$\xi_1 = \begin{bmatrix} 0 \\ 0 \\ 0 \\ 0 \\ 0 \\ 2.54 \end{bmatrix}, \xi_2 = \begin{bmatrix} 0 \\ 9.93 \\ 0 \\ 0 \\ 0 \\ 2.54 \end{bmatrix}, \xi_3 = \begin{bmatrix} 0 \\ v+8.57 \\ 3.56 \\ -2.54 \\ 0 \\ 0 \end{bmatrix},$$

$$\xi_4 = \begin{bmatrix} 0 \\ -v-8.57 \\ -3.56-ua \\ 2.54 \\ 0 \\ 0 \end{bmatrix}, \xi_5 = \begin{bmatrix} 6.86+ua \\ -.23 \\ 0 \\ 0 \\ 0 \\ 2.54 \end{bmatrix}, \xi_6 = \begin{bmatrix} v+8.57 \\ 0 \\ .23 \\ 0 \\ 2.54 \\ 0 \end{bmatrix},$$

$$M = \begin{bmatrix} I_{3,3} & q_{t,0} \\ 0_{1,3} & 1 \end{bmatrix}, q_{t,0} = \begin{bmatrix} .23 \\ 13.86+ua \\ -v-21.96+\text{tip} \end{bmatrix}.$$

The initial location of the tip of the forearm is $q_{t,0}$, the angular displacements measured by the potentiometers were $\theta_i$. The length of the upper arm is ua, and the vertical displacement at the shoulder is v. (All kinematic equations are in cm.)

Data Acquisition:

Voltage signals are acquired from T-WREX's position sensors 22 using a PCI data aquisition card (Measurement Computing, PCI-DAS6013). Data can be acquired at 66 Hz per channel through the software interface.

Measurement Accuracy:

To evaluate the measurement accuracy of the modified T-WREX 10, we measured the ability of the system 10 to measure known locations in space, using a scale placed near the vertical mid-plane of the workspace on a table near the end of the depth of range, a vertical disk in the middle of the workspace. The resolution for position measurement was within ±0.38 cm.

Grip Sensor

To incorporate hand grasp into therapy activities, we attached a custom-made, pressure-sensing, handgrip 20 to the orthosis. The handgrip 20 is comprised of a hydraulic bladder made of 2.54 cm diameter marine grade polyolefin tubing, shrink-wrapped around PVC pipe ends connected via an aluminum rod that is tapped with a small bore hose fitting. Small diameter tubing connects the bladder to a pressure transducer (not shown—Viatran Corp., 2476AHG, 0-50 PSIG) mounted at the back of the wheelchair. The transducer detects grasp pressures up to about 345 kN/m$^2$ (with a resolution of approximately 2.0 kN/m$^2$, or 2% of the peak maximum grip pressure of an average adult male, 110 kN/m$^2$ [20]).

Software Enhancements

Java Therapy and T-WREX

We have earlier developed a software controlled methodology under the name, Java Therapy, as a first-step toward home-based training. See D. Reinkensmeyer, et. al. "Java Therapy: Web-Based robotic rehabilitation," in *Integration of Assistive Technology in the Information Age*, vol. 9, *Assistive Technology Research Series*, M. Mokhtari, Ed. Amsterdam: IOS Press, 2001, pp. 66-71. Java Therapy used a force feedback joystick to assist or resist in movements of the hand in a small workspace, and a web-based software system to remotely specify movement exercises and track progress. While very low-cost, Java Therapy's small workspace movements were not closely related to the types of functional movements which stroke survivors wished to improve, such as reaching, eating, dressing, and washing.

We therefore developed an improved input device for Java Therapy by modifying an anti-gravity arm orthosis, the Wilmington Robotic Exoskeleton (WREX). WREX was originally designed to help children with weakened arms to perform activities of daily living, such as eating. WREX uses elastic bands, wrapped around two four bar mechanisms, to counterbalance the arm. See Tariq Rahman et. al., "A body-powered functional upper limb orthosis", Journal of Rehabilitation Research and Development Vol. 37 No. 6, September/October 2000. WREX is a five degrees-of-freedom, back drivable, passive device. It allows naturalistic movements across an estimated 66% of the normal workspace of the arm in the vertical plane and 72% in the horizontal plane. Thus, it is well suited for measuring functional arm movement. In addition, because it counterbalances the weight of the arm, it could potentially allow even a severely weakened stroke patient to practice functional arm movements at home, without the safety concerns raised by an active robotic device.

The original version of the Java Therapy software (Java Therapy 1.0) required that users have an active connection with the Internet and a remote computer network 14a. Modified Java Therapy 2.0 is an ASP platform solution that stores and displays patient progress of T-WREX exercises in both web and standalone versions with an identical user interface. The web version is served through a server running IIS services and website hosting. This version is suitable for use by patients with high bandwidth Internet access or multiple phone lines. The standalone version is accomplished by the use of what is called a loop back to serve essentially the same version of the software, and does not require an Internet connection.

To use Java Therapy 2.0 the user must first log into a home page through Internet Explorer. Once the subject has logged into the system, the program displays a "To Do List" of games to choose from, with a required minimum number of repetitions per day to complete for each game.

Our criteria for selecting the Java Therapy 2.0 games were that they be functionally relevant and quantifiable with the modified T-WREX system 10. A summary page is displayed at the end of each game that shows the user their current score and how their score compares to their most recent attempt, and the mean of all of their previous attempts. The games and outcome scores in the illustrated embodiment are as follows.

"Shopping" requires the user to move a hand cursor by moving the arm up, down, left and right to a common household item (e.g. a can of food) displayed on a picture of shelves, squeeze the handgrip 20 above a threshold pressure to grab the object, move the item to the shopping cart, and release the handgrip 20 to drop it in. The grasp function can be turned off if the subject is too weak to reliably pass the grip threshold. The shopping score that is displayed to the user following completion of the game is the number of items placed in the cart divided by the game duration.

The system 10 includes an computerized adjustment means or software to automatically adapt the range of motion and grip force threshold level required to successfully perform the simulated activities of daily living. Specifically, the computer quantifies the user's ability to perform a task, and then based on that quantification, expands or shrinks the required range of motion appropriately, and raises or lowers the grip threshold appropriately, so that the user can complete the task successfully. For example, for the shopping game, if the user reaches all of the items successfully, then the next time he plays the game, the computer adjusts the sensor scaling so that reaching for the items requires movement of the user's arm through a slightly greater range of motion. If the user does not reach some items, then the computer adjusts the sensor scaling so that reaching for the items requires movement of the user's arm through a slightly smaller range of motion from the user. In this way, the system always adapts its parameters to try to make the tasks "difficult but doable", maintaining both challenge and motivation in the therapy. In the same way, if the subject has difficulty grasping an object in the shopping game, the system lowers the grasp threshold slightly until the subject is able to grasp the object. If the subject succeeds in grasping the objects quickly, then the system raises the grasp threshold to challenge the subject more.

"Washing the Stove" requires the user to move the arm across the horizontal plane to "clean away" an array of broken eggs spread across the stove. The score is the number of eggs cleared divided by the game duration.

"Cracking Eggs" requires the user to move their hand across the horizontal plane to the location of an egg displayed on the screen, and then squeeze the handgrip causing the egg to attach to the hand cursor. If the subject squeezes the handgrip 20 with a pressure above a therapist-set threshold, then the egg breaks. The subject must then move the egg over a frying pan and squeeze with a force above a defined threshold to crack the egg into the pan. The game score is the number of eggs cracked in the pan divided by the game duration.

"Washing the Arm" requires the user to perform a washing-like motion across the upper segment of their unimpaired arm. The computer first prompts the user to move their impaired arm near their unimpaired shoulder and click the mouse with their unimpaired hand. The computer stores the selected location. The computer then prompts the user to move the impaired hand near the unimpaired-elbow and store the location. The user then practices making movements between the two points, mimicking washing their arm. The user must move to within 5 cm of the stored targets to consider the movement completed. The computer screen shows the user a live video of himself as feedback, acquired from a low-cost digital camera mounted on the computer monitor, as well as a cartoon figure from which dirt disappears with each successful washing movement. The score is the number of completed movements divided by the game duration.

"Eating" is similar to "Washing the Arm" except the computer prompts the user to store one point near the mouth and one near the lap. The user then practices making movements between the two points, mimicking eating. The computer screen shows the user real-time video acquired from the camera mounted on the computer monitor, as well as a plate from which food disappears gradually. The score is the number of completed movements divided by the game duration.

"Making Lemonade" requires the user to squeeze the handgrip 20 as hard as possible for a chosen duration. The computer screen displays a pitcher of lemonade filling in proportion to the integrated pressure transducer voltage signal. The integrated pressure signal divided by the game duration is the score.

"Ranging the Arm" requires the user to move their arm as far up, down, left and right as possible. The game shows the subject an aesthetic image that is uncovered in proportion to their range of horizontal and vertical range of motion. The score is the exposed area of the image divided by game duration.

It must be understood that many other daily task of living or special therapy motions can be substituted for the examples provided above without departing from the spirit and scope of the invention. The few examples given by no means exhaust the number of possibilities that can be included.

Device Testing Methodology

We performed two studies of the system's capabilities with nine chronic stroke subjects. The subject selection criteria for both studies were a minimum of six months post stroke, no shoulder pain, ability to comprehend and communicate about the required tasks, and some degree of arm impairment (Fugl-Meyer Motor Score for the Upper Extremity<56 out of 66). For all experiments, the subjects were seated with a shoulder harness to prevent torso movement, and the subject's arm was placed in the padded orthopedic splint attached to modified T-WREX 10.

Figure 2A:
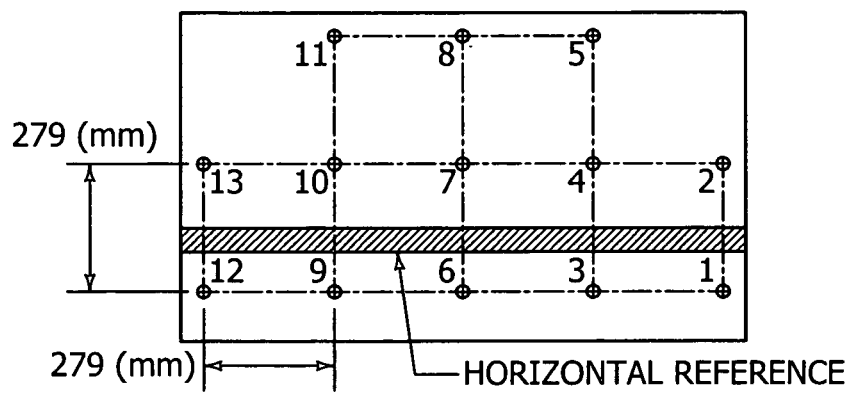
FIGS. 2a and 2b are diagrams of a test fixture for measuring the force required to hold the arm in different positions when the orthosis provided gravity balance to the arm, and when it did not.
Figure 2B:
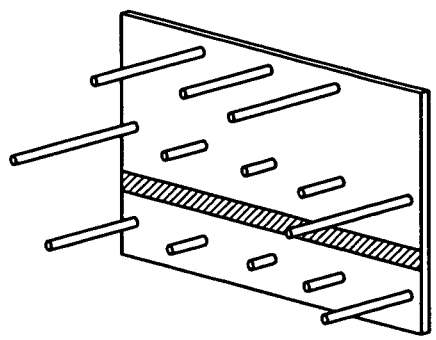

Study One—Effect of Gravity Balance on Static Positioning of the Arm and Voluntary Arm Movements:

We quantified how well the gravity-balancing function of the orthosis worked by first measuring the forces required for a therapist to statically position the arm with and without gravity balance "on". In the gravity balance "on" condition, the combined weight of the subject's arm and orthosis was balanced by adding rubber bands to the orthosis until the arm "floated" in a default configuration. The default configuration was the elbow flexed to 90 degrees and the shoulder flexed such that the forearm was parallel to the floor and the upper arm was parallel to the parasagittal plane. In the gravity balance "off" condition, the weight of the orthosis itself was counterbalanced with the elastic bands, but not the weight of the arm. For the static positioning tests, we measured the force required to hold the subject's relaxed arm at points throughout its workspace. Specifically, a physical therapist held the subject's arm at thirteen targets or pegs mounted on a test fixture or board that was placed at the workspace boundary as diagrammatically illustrated in FIG. 2a with the order of presentation of the gravity balance "on" and "off" conditions randomized. While grasping the force-torque transducer, the therapist held the distal end of T-WREX to the tip of each rod that protruded from the fixture. The "Horizontal Reference" on FIGS. 2a and 2b indicates the vertical level at which the arm was placed when setting the number of rubber bands for the gravity counterbalance. The targets were selected to be at the workspace boundary because this situation represented the "worst case" for gravity balance. That is, the arm was perfectly balanced in the default configuration near the sternum. Since the required level of counterbalance is position-dependent, fully extending the elbow generates the largest change in moment possible, with respect to the accurate counterbalance in the default configuration. The subject was instructed to attempt to relax the arm during testing. The shoulder 24 of the modified T-WREX 10 was aligned with the center of the test fixture and placed 84 cm in front of it. The therapist held the subject's arm by grasping a six-axis force-torque sensor (ATI, Industrial Automation, FT-3293) that was mounted to the orthosis beneath the forearm brace. The sensor was sampled by the computer at 60 Hz. Both the impaired and unimpaired arms of each subject were tested using this protocol. The mean Fugl-Meyer score for the four subjects who participated in this experiment was 19.3 (±6.5 SD).

To quantify the effect of gravity balance on voluntary arm movements, we measured how well nine hemiparetic subjects could perform various arm movements while they wore the orthosis with and without gravity balance. The subjects' mean Fugl-Meyer score was 25.1 (±13.9 SD). Three types of movement tests were performed, with the order of presentation of the gravity balance "on" and "off" conditions randomized. The first test was a subsection of the arm Fugl-Meyer score that could be performed while the subject's affected arm was in the orthosis. This modified Fugl-Meyer test measured fourteen tasks with a possible total score of twenty-eight. The second test assessed reaching movements. The subjects reached eight times to two targets located at the boundary of the arm's passive workspace, one on the ipsilateral side and one on the contralateral side, at the height of the subject's chest. The subjects also reached upwards from the lap to the highest possible point eight times. The third test assessed drawing movements. Four subjects traced a circular pattern (diameter of 17.8 cm) presented on a transparent plastic disc in the vertical plane, centered in front of them, 5 fist widths from the front of the affected shoulder. Each subject was asked to hold their arm up to the start point with their unimpaired arm before starting each movement. The subjects repeated the circle tracing task thirty times in intervals of ten with one minute rests in between each interval.

Data Analysis:

Data from the left arm was flipped in a mirror-symmetric fashion so that all data was analyzed in a right arm coordinate frame. Paired, one-sided t-tests with a significance level of 0.05 were used to determine whether the static positioning force from the force ranging test, the subset of the Fugl-Meyer score, the range of motion to the targets, and the maximum vertical reach changed with gravity balance.

The data from the circle tracing task was analyzed by calculating three measures of the success in achieving the task. The Radius Error was computed as the difference between the actual and the desired radius for each point sampled during tracing. Circularity was computed as the standard deviation of the Radius Error. The Circle Percentage Completed was computed by dividing the circle into 64 sectors, then computing the percentage of sectors in which at least one sampled point occurred. A paired, one-sided t-tests comparing gravity balance "on" to "off" across all thirty reaching trials was conducted for each subject to determine improvement in the subjects' ability to trace circles for each of the three success measures.

Study Two—Effect of Gravity-Assisted Movement Training on Arm Motor Recovery:

The second study was designed as a pilot study to test the feasibility of using the modified T-WREX 10 as a tool for retraining arm movement after chronic stroke. We tested the hypothesis that repetitive movement training with modified T-WREX 10 over a two month period would improve the ability of chronic hemiparetic stroke subjects to move their arm and hand. Five hemiparetic subjects were enrolled in the study (Table 1), all of whom had severe arm and hand impairment.

Training Protocol:

The five subjects practiced movement training with the orthosis for 45 minutes, three times per week, for eight consecutive weeks. One subject completed only 15 instead of 24 training sessions for personal reasons not related to the study. In each training session, a physical therapist or research assistant assisted the subjects to place their affected arm in the orthosis. The set-up time was typically 3 minutes. The subjects then used the Java Therapy 2.0 software to complete the seven therapy games three times per session. The duration of all games was 3 minutes, except for the "Making Lemonade" and "Ranging the Arm" games, which lasted 15 seconds and 1 minute respectively. The therapist or the research assistant provided occasional verbal cueing or manual assistance to the subjects as they played the games during the first week. By the second week of therapy sessions, subjects seldom required manual assistance or verbal cueing during the 45 minute Java Therapy session.

Weight-Support Progression:

Subjects experienced a decreasing amount of weight support for their arms throughout the study. For the first two weeks, the number of rubber bands chosen was such that it balanced the arm in the default configuration used in Study One. For weeks three and four 20% of the rubber bands were removed. For weeks five and six, another 20% of the rubber bands were removed. Rubber bands were not removed for weeks seven and eight due to the difficulty the subjects experienced performing the tasks with the existing 40% reduction in gravity balance.

Outcome Measures:

Subject's movement ability was evaluated before and after the eight-week movement training program using four clinical tests: the Fugl-Meyer Motor Assessment for the Upper Extremity, the Rancho Functional Test for The Hemiplegic/Paretic Upper Extremity, the Box and Blocks Test for Manual Dexterity, and a modified version of the Blocks and Box test in which the subjects attempt to move their arm back and forth across a divider without picking up blocks.

Subject's movement ability was also evaluated using several quantitative measures at each therapy session. The subjects' grip strength was tested at the beginning and end of each training session. Grip strength was tested using a hydraulic hand dynamometer (Jamar, 5030J1) while the subject was seated, with the arm supported on their lap. The subjects' ability to reach to a target in three-dimensional space without any arm support, and to reach across a table top with arm support to a target, were also tested before each training session using a three degrees-of-freedom lightweight robot arm (PHANToM 3.0 SensAble Technologies, Inc., Woburn, Mass., USA) with a customized orthopedic hand-splint interface. The subjects' arm pain was assessed by ask-

TABLE 1

| Subject No. | Age and Gender | Paretic Side | Years Post Stroke PRE | Tone/Ashworth scale PRE | Fugl Meyer (of 66) PRE | Fugl Meyer (of 66) DELTA | Rancho-Level PRE | Rancho-Level DELTA | Rancho-Tasks performed at next level PRE | Rancho-Tasks performed at next level DELTA | Box & Blocks PRE | Box & Blocks DELTA | Mod. Box & Blocks PRE | Mod. Box & Blocks DELTA |
|---|---|---|---|---|---|---|---|---|---|---|---|---|---|---|
| 1 | 72 F | Left | 3 | 4 | 11 | 5 | 3 | 0 | 0 | 0 | 0 | 0 | 0 | 0 |
| 2 | 70 M | Left | 6 | 4 | 19 | 5 | 2 | 1 | 1 | 0 | 0 | 0 | 0 | 0 |
| 3 | 43 F | Left | 9 | 3 | 27 | 3 | 3 | 0 | 0 | 0 | 0 | 0 | 19 | 0 |
| 4 | 44 F | Right | 4 | 3 | 20 | 8 | 3 | 0 | 0 | 0 | 0 | 1 | 15 | 7 |
| 5† | 72 M | Right | 11 | 3 | 32 | 4 | 3 | 0 | 0 | 2 | 0 | 0 | 0 | 0 |
| AVG | 60.2 | | 6.6 | 3.4 | 21.8 | 5.0* | 2.8 | 0.2 | 0.2 | 0.4 | 0.0 | 0.2 | 6.8 | 1.4 |
| STD | 15.2 | | 3.4 | 0.5 | 8.0 | 1.9 | 0.4 | 0.4 | 0.4 | 0.9 | 0.0 | 0.4 | 9.4 | 3.1 | ing the subjects to define the pain intensity on a scale from one to ten, with one being no pain and ten being severe pain. Blood pressure and pulse rate were measured before and after each training session.

Data Analysis:

Changes in the clinical scores post-training compared to pre-training were analyzed using paired t-tests for each subject. The percent of reaching range was calculated by first subtracting out the baseline range (distance moved on first day) and then dividing by the distance from the start point to the target. Linear regression was used to determine if there was a significant change in the percentage range of motion of supported, unsupported reaching, and grip strength, as a function of training sessions. The average change in these measures across training was estimated using the slope of the best-fit line.

Changes in game scores with training were analyzed for three games only (Shopping, Ranging the Arm and Cleaning the Stove) due to a data storage error with the other two games. The scores for these games were normalized to a scale of 0 to 1 by dividing the scores by the score of an unimpaired user, and then averaged to obtain a single score. Linear regression was used to determine if there was a significant change in the normalized game score for the four-week period during which the gravity balance was held at a fixed level of 60%.

Results

Figure 3A:
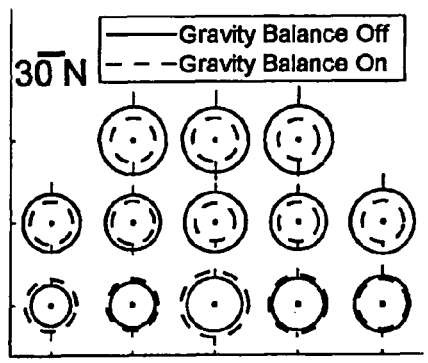
FIGS. 3a and 3b depict the mean effect of gravity balance across four subjects. The circle radius is the magnitude of force required to hold the subjects' arms at the test fixture locations shown in FIG. 2a. The vertical bars indicate one standard deviation across subjects.
Figure 3B:
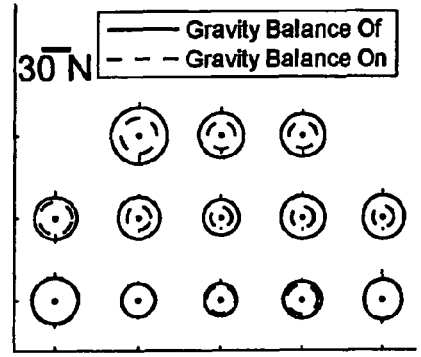

Study One: Effect of Gravity Balance on Static Positioning of the Arm and Voluntary Arm Movements We first measured the force required to hold the arm in different positions when the orthosis provided gravity balance to the arm, and when it did not. The magnitude of force required to hold the arm at the boundary of its workspace was significantly smaller with gravity balance "on" than with it "off", for all of the unimpaired arms and three of the impaired arms of the four subjects tested (t-test across thirteen targets, $p<0.04$ for each subject, as graphically illustrated in FIGS. 3a and 3b). The gravity balance function was more effective for workspace locations above the horizontal reference shown in FIG. 2, and ineffective for those locations below it (FIG. 3). When we compared the force required to hold the impaired arm with that required to hold the unimpaired arm, a significantly greater force of 9.6 N (±4.6 SD) was required for the impaired arm, consistent with increased tone (paired t-test across subjects, $p<0.001$).

Figure 4A:
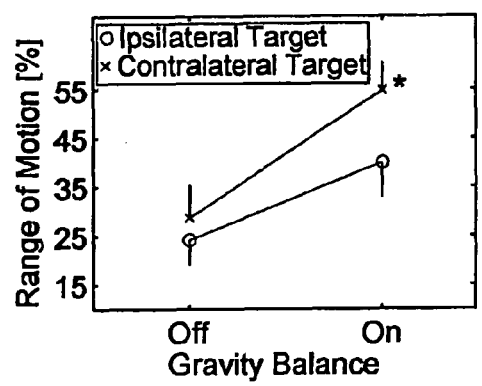
FIGS. 4a-4c illustrates the effect of gravity balance on reaching movements for nine subjects.
Figure 4B:
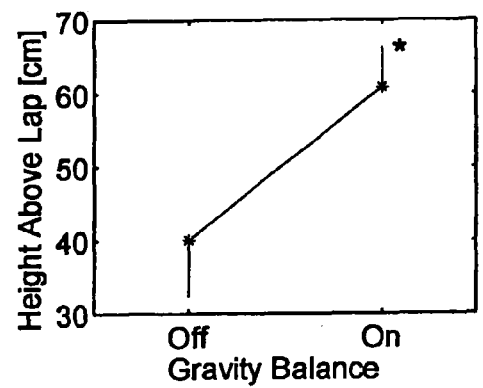
Figure 4C:
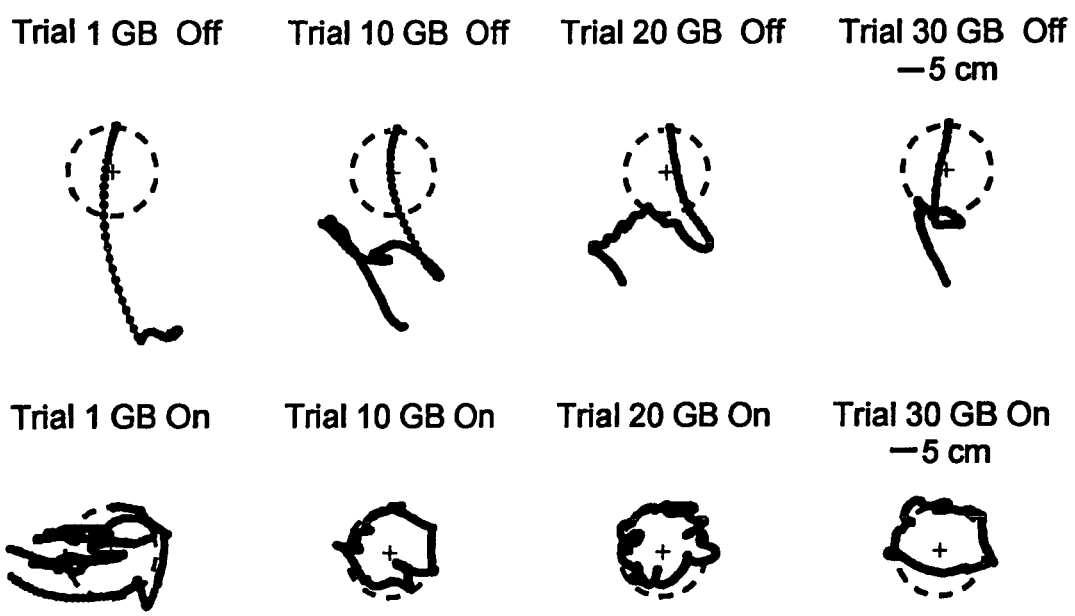

The subjects moved more effectively with the gravity balance "on". The mean modified Fugl-Meyer score with gravity-balance was 12.1 (±6.2 SD) and without gravity-balance was 11.3 (±6.3 SD), a difference that neared significance (paired, one-sided t-test, $p=0.055$). Gravity balance significantly improved reaching to the contralateral target (paired, one-sided t-test, $p=0.038$), but not to the ipsilateral target ($p=0.071$, FIG. 4a). Gravity balance significantly improved the vertical reaching range of motion ($p=0.008$, FIG. 4b). Finally, gravity balance significantly improved the ability of the subjects to draw circles for those subjects who could not draw them without assistance (FIG. 4c), and improved the quality of the drawn circles for those who were able to draw a circle (paired t-test for each subject, $p<0.05$, Table 2).

TABLE 2

| Subjects Fugl-Meyer | Mean radius error area | | Mean radius error p-value | Circularity measure area | | Circularity p-value | % Circle completed area | | % Circle completed p-value |
| --- | --- | --- | --- | --- | --- | --- | --- | --- | --- |
| | GB-Off | GB-On | | GB-Off | GB-On | | GB-Off | GB-On | |
| 19 | 15.00 | 3.43 | 0.001* | 34.50 | 14.80 | 0.001* | 100.00 | 100.00 | 1.000 |
| 20 | 47.00 | 13.20 | 0.001* | 97.30 | 18.20 | 0.001* | 32.69 | 100.00 | 0.001* |
| 18 | 29.80 | 21.60 | 0.006* | 40.10 | 30.20 | 0.001* | 80.69 | 100.00 | 0.001* |
| 54 | 3.04 | 2.28 | 0.002* | 11.40 | 8.69 | 0.008* | 100.00 | 100.00 | 1.000 |

Study Two: Effect of Gravity-Assisted Movement Training on Arm Movement Ability

The five subjects who participated in the two month therapy program significantly improved their arm movement ability as measured by the Fugl-Meyer score (one-sided t-test, $p=0.002$, Table 1). The mean improvement was 5 points (±1.87 SD). The improvement in the Fugl-Meyer Score was primarily due to improvements in sub-scores related to shoulder movement (Table 3). No significant improvements were seen for the three functional tests: the Rancho Functional Test, the Box and Blocks test, or the modified Box and Blocks test.

TABLE 3

| | Elbow (%) | Shoulder (%) | Total (%) |
| --- | --- | --- | --- |
| 0-1 | 17 | 26 | 43 |
| 1-2 | 17 | 35 | 52 |
| 0-2 | 4 | 0 | 4 |
| Total (%) | 38 | 61 | |

Figure 5A:
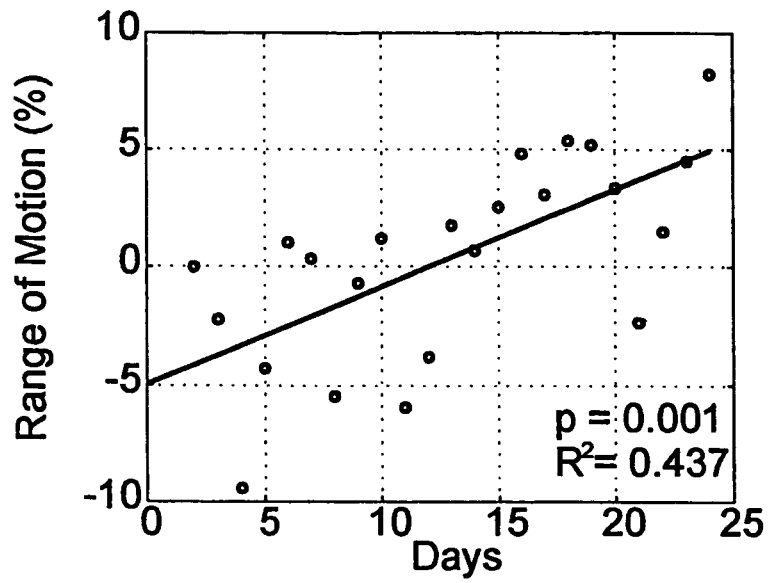
FIGS. 5a and 5b are graphs illustrating the mean range of motion of unsupported reaching and normalized game scores across the 24 training sessions (Study Two).
Figure 5B:
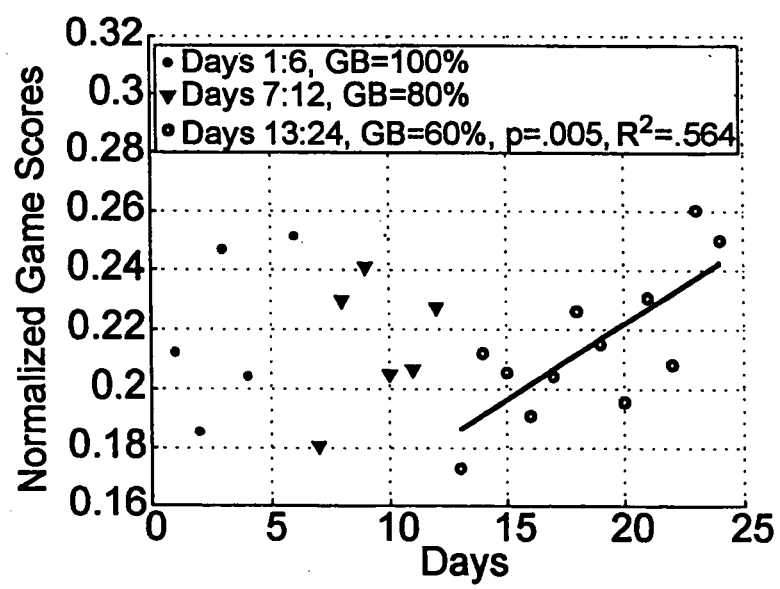

At each therapy session we measured the subject's grip strength, ability to reach to a target, self-rating of pain, and vital signs. Grip strength significantly increased for two of the five subjects over 24 therapy sessions (linear regression, $p<0.05$, Table 4). Three of the subjects significantly improved the distance that they could reach away from their body both with and without support (Table 4). The mean percent improvement in unsupported reach extent, as calculated from the linear regression in FIG. 5a, was 9% which amounted to a 3.3 cm increase on average. There were no significant changes in the pain score, pulse rate, or blood pressure across the training program, or when these measures were compared before and after each training session.

TABLE 4

| | Supported Table Reaching Range | | | Free Reaching Range | | | | Hand Grip Strength | | | | |
|---|---|---|---|---|---|---|---|---|---|---|---|---|
| Subject | Change in Distance Reached (mm) | $R^2$ | p-value | Change in Distance Reached (mm) | Change in Distance Reached (%) | $R^2$ | p-value | Initial Grip Strength | Change in Grip (kgF) | % Change | $R^2$ | p-value |
| 1 | 64 | 0.09 | 0.200 | 11.12 | 3.05 | 0.05 | 0.332 | 1 | 1.95 | 195.00 | 0.06 | 0.245 |
| 2 | 123 | 0.47 | 0.001* | −4.26 | −1.17 | 0.01 | 0.651 | 2 | 3.26 | 163.00 | 0.15 | 0.065 |
| 3 | 35 | 0.25 | 0.029 | 76.10 | 20.88 | 0.35 | 0.006* | 1 | 2.68 | 268.00 | 0.33 | 0.003* |
| 4 | 124 | 0.74 | 0.001* | 45.19 | 12.4 | 0.21 | 0.042* | 6 | −0.16 | −2.67 | 0.00 | 0.906 |
| 5† | −13 | 0.09 | 0.359 | 32.95 | 9.04 | 0.21 | 0.034* | 15 | 5.996 | 39.97 | 0.64 | 0.001* |
| AVG | 66.6** | | | 32.2** | 8.8** | | | | 2.7** | 132.7** | | |
| STD | 58.8 | | | 31.1 | 8.5 | | | | 2.2 | 111.8 | | |

The subjects improved the scores they achieved on the games during the last four weeks of training, when the level of gravity balance was held fixed at 60%. The mean, normalized, game score across three games increased significantly by 5.6% (FIG. 6-B, linear regression, $R^2=0.564$, p=0.005).

The force of gravity severely limits arm movement ability for many stroke patients. To allow stroke patients to practice arm movement training we instrumented a gravity-balancing orthosis, coupled a pressure sensing handgrip 20 with the orthosis, and developed simple virtual reality software that simulates functional movement tasks and provides quantitative feedback of performance.

Study One demonstrated that stroke patients who have not practiced moving their arm in a coordinated manner for several years can quickly relearn to control their arm movement given some support against gravity with this system. For example, the subjects were able to trace a circle in the vertical plane with gravity support even though their ability to do this was severely limited without gravity support. Gravity-balance also improved reaching range of motion.

The results of Study Two further demonstrated that this latent ability to coordinate arm movement can be enhanced with repetitive training with the modified T-WREX 10, resulting in improvements in unsupported arm movement ability. Subjects who practiced with modified T-WREX 10 over an eight week period improved their movement ability as quantified by the Fugl-Meyer score, hand grasp strength, as well as unsupported and supported reaching range of motion. They achieved these improvements with approximately six minutes of direct contact with a rehabilitation therapist, focused on donning or doffing the device, and forty-five minutes of repetitive movement training with T-WREX.

These results demonstrate the safety and feasibility of automating functional, upper-extremity rehabilitation therapy for chronic stroke patients using passive gravity assistance and a grip sensor to execute a sequence of simulated, daily tasks. We will first discuss the significance of these results in relationship to other attempts to automate movement training after stroke and then discuss directions for future research.

Comparison with Other Attempts to Automate Movement Training

The approach we adopted in this study to automate movement training is different from previous clinical and robotic approaches in several ways. It is different from the clinical use of devices such as arm skateboards, overhead slings, and mobile arm supports due to the use of an instrumented orthosis with a large, three-dimensional workspace. The use of an instrumented device makes it possible to provide quantitative feedback to the patient and therapist about movement recovery, and also engages the user in simple virtual reality games oriented towards improving functional activities. The large workspace makes a greater range of movement possible than with standard clinical devices. Clinical devices for supporting the arm also do not include grip force sensors.

This approach is different from recent attempts to use robotic devices to automate therapy, such as U.S. Pat. No. 5,466,213 because it uses a passive device that does not generate power. The system can be manufactured at substantially less cost than an equivalent actuated system. Although preliminary testing of robotic devices has shown that they too can be safe, the modified T-WREX 10 has an obvious safety advantage compared with robotic approaches because it is fundamentally incapable of moving on its own. This advantage may be especially significant if the technology is to be used for home based therapy. Kinematically, the system 10 allows a substantially larger range of motion than previous robotic devices, including feeding and washing motions, contributing to its ability to facilitate functional movements. The incorporation of a simple hand grasp sensor with an arm supporting mechanism is unique to our knowledge, and again contributes to the ability of the system to facilitate functional movement.

On the other hand, the system is more costly than standard clinical assistive devices because of its mechanical complexity, and use of sensors and a computer. The system is also less flexible than robotic approaches because it is limited in the pattern of assistive force that it can apply. The modified T-WREX 10 can only apply fixed levels of gravity support, defined by the number of elastic bands attached to the device. Further, the gravity support mechanism is only partially effective in counterbalancing the arm. Specifically, the arm can be perfectly balanced in any one configuration. However, when it is moved away from such a configuration, the counterbalance accuracy degrades. The system 10 also does not compensate for subject-specific variations in muscle tone. Further, the device does not allow changes in forearm supination or pronation away from the initial forearm orientation, or the full range of shoulder internal and external rotation.

The system 10 is also different from the recently-developed Auto-Cite system, which consists of a computer-adjustable workspace with sensorized tasks for automating constraint-induced therapy. Auto-Cite focuses on hand manipulation tasks suitable for less impaired stroke patients and does not provide assistive support to the arm. The system we developed is targeted at severely impaired stroke patients, as it allows individuals with only a small amount of arm and hand movement ability to engage in simulated functional activities.

The clinical viability of this approach will depend in large part on the system's effectiveness in facilitating movement gains. Training with the modified T-WREX 10 for eight weeks did not improve the subject's functional movement ability according to the scales used here. The lack of improvement in the functional scales is likely due to a floor effect in these scales: i.e. these scales are insensitive to small changes in movement ability when the starting ability level is low. The five point mean improvement in the impairment-measuring Fugl-Meyer score, on the other hand, was comparable to improvements seen in patients with a similar degree of deficits with the MIT-MANUS (4.2 additional points with robot therapy), MIME (3.4 point gain with robot therapy, 1.6 point gain with conventional therapy), and GENTLE/s (4 point gain with robot therapy). The majority of improvement in the Fugl-Meyer Score was seen in the shoulder (61% increase) as compared to the elbow (38% increase) (Table 3), similar to the improvements seen with the robot therapy group and conventional therapy control group in the MIME study (Robot: Shoulder-65%, elbow-35%; Control: Shoulder-69%, elbow-31%), and the robot therapy group in the GENTLE/s study (Shoulder-55%, elbow-45%). This relatively greater improvement in shoulder movement could be due to an inherent proximal-to-distal pattern of recovery, or to a greater emphasis on shoulder-related exercises due to the selection of the training games. Incorporating games that encourage practice of isolated elbow movement is an important direction for further development.

Practice with the modified T-WREX 10 also improved quantitative measures of upper extremity movement ability. Three subjects improved their ability to reach to a target with and without support. The gain in free reaching range of motion was approximately 3 cm on average, with one subject achieving a 7.6 cm gain (Table 4). Reaching in free space away from the body requires substantial shoulder strength because the center of mass of the arm moves away from the body during such movements, producing a large moment at the shoulder. The gains in shoulder sub-scores for the Fugl-Meyer score are thus consistent with the observed gain in reaching range of motion. Subjects in the MIME study also improved their reaching range of motion by an average of 5 cm.

Two subjects significantly improved their hand grasp strength by 270% (2.7 kgF) and 40% (6.0 kgF), respectively. Subjects who underwent movement training with the MIT-MANUS device did not significantly improve their hand function over the control group suggesting that motor gains are specific to the limb segments exercised. The present results indicate that arm movement training can be integrated with hand movement training, producing benefits for both the arm and hand.

None of the daily measures, including hand grasp strength, reaching range of motion, and the game scores, appeared to have reached a plateau during the training program. This suggests that additional improvement may have been possible with continued training. Defining the limits to the level of recovery possible with intensive practice is an important direction for future research.

Exit interviews with the subjects indicated that they increased their use of their affected side in some activities of daily living. Two subjects began carrying items such as laundry or bags with their affected side following training. Another subject noted that increased range of motion enabled her to turn on and off a light switch with the affected side. On a scale from 1 to 5, 1 being the least enjoyable, 5 being well satisfied, the subjects on average rated their enjoyment of using the device with a score of 4.3. A common criticism from the subjects was that the device should be refined to allow supination and pronation of the forearm.

These pilot study results indicate that the T-WREX training system can produce measurable benefits in arm movement ability of chronic stroke patients. Incorporating forearm supination and pronation along with shoulder internal and external rotation is included within the scope of the invention and allows the system 10 to assist in even more naturalistic arm movements.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following invention and its various embodiments.

It must be understood that different arm supports could be substituted, such as the Swedish sling, JAECO arm support, an arm skateboard, and a table with a towel on it different grasp sensors could be used (goniometers), and different types of computer displays could be used (VR display, projection onto table, audio feedback on successful completion of the movement). Each of these substitutes in all possible combinations is expressly considered as within the scope of the invention.

Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the invention is explicitly contemplated as within the scope of the invention.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. An apparatus for upper limb rehabilitation training of coordinated arm/forearm and grasping movements of a patient comprising:

a spring-actuated counterbalanced arm/forearm support which is an articulated exoskeleton worn by the patient and coupled to a stand relieving at least a portion of the weight of an arm and forearm of the patient and to increase the range of movement of the arm and forearm with at least three degrees of freedom to simulate multi-joint coordination exercises that require coordination of the arm and hand, wherein the portion of the weight of the arm and forearm is relieved from the patient during the entire simulation of the multi-joint coordination exercises;

a plurality of arm/forearm measurement sensors coupled to the arm/forearm support capable of measuring joint angles of the impaired arm and forearm movements of the arm/forearm of the patient;

a sensor capable of measuring impaired grasping force or measuring impaired movement of a hand of the patient;

a computer coupled to the arm/forearm measurement means and the grasping measurement means to process measurements of impaired arm/forearm and grasping movements to control a graphical representation of the arm/forearm and grasping force in interaction with a virtual environment, and to provide a visual feedback signal to the patient of simulated multi-joint coordination exercises that require coordination of the arm and hand performed with enhanced motor ability relative to the actual impaired motor ability; and a display device coupled to the computer to display the visual feedback signal of the simulated multi-joint coordination exercises that require coordination of the arm and hand, wherein motivation of the patient to perform the upper limb rehabilitation movement training is provided despite limited motor ability.

2. The apparatus of claim 1 where the support comprises an adjustment means for varying a force level required to move the arm and forearm, and where the computer automatically adjusts a plurality of parameters according to patient completion of the simulated multi-joint coordination exercises that require coordination of the arm and hand, wherein the computer further comprises means for automatically varying a range of movement of the arm and forearm required to successfully perform the simulated multi-joint coordination exercises that require coordination of the arm and hand based upon previous patient performance.

3. The apparatus of claim 1 where the computer comprises an adjustment means for automatically varying a threshold level of the grasping force and releasing movement required to successfully perform the simulated multi-joint coordination exercises that require coordination of the arm and hand based upon previous patient performance.

4. The apparatus of claim 1 where the spring-actuated counterbalanced arm/forearm support comprises an elastic suspension and a five degrees-of-freedom mechanism which counterbalances the weight of the arm/forearm using the elastic suspension.

5. The apparatus of claim 1 where the spring-actuated counterbalanced arm/forearm support comprises means for performing multi-joint coordination exercises that require coordination of the arm and hand in the virtual environment.

6. The apparatus of claim 1 where the spring-actuated counterbalanced arm/forearm support comprises a five degrees-of-freedom, back-drivable mechanism using elastic bands wrapped around two four bar linkages to counterbalance the arm/forearm.

7. The apparatus of claim 1 where the spring-actuated counterbalanced arm/forearm support has a distal tip and a plurality of movement axes, and where the arm/forearm measurement sensor provides measurement resolution of the distal tip of the spring-actuated counterbalanced arm/forearm support sufficient to allow individuals with severe weakness to simulate multi-joint coordination exercises that require coordination of the arm and hand in a virtual reality environment.

8. The apparatus of claim 1 where the arm/forearm measurement sensor measures impaired arm and forearm movements without initial zeroing, so that no initialization procedures are required.

9. The apparatus of claim 1 where the grip sensor measures impaired grasping force and releasing movement without initial zeroing, so that no initialization procedures are required.

10. The apparatus of claim 1 where the hand gripper comprises a fluidic bladder and the grip sensor comprises a pressure sensor coupled to the bladder.

11. The apparatus of claim 1 further comprising a remote computer network coupled to the computer from which network the computer is controlled to adjust the parameters of a plurality of simulated multi-joint coordination exercises that require coordination of the arm and hand.

12. The apparatus of claim 1 where the computer generates quantitative feedback of performance.

13. The apparatus of claim 1 where the computer generates a rehabilitative therapy and therapeutic history of performance.

14. The apparatus of claim 1 where the spring-actuated counterbalanced arm/forearm support facilitates forearm/forearm supination and pronation, elbow flexion and extension, in combination with shoulder internal and external rotation, flexion and extension, and abduction and adduction.

15. An apparatus for automating upper-extremity rehabilitation therapy for a motor impaired stroke patient comprising:

a spring-actuated counterbalanced gravity assistance articulated exoskeleton worn by the patient and coupled to a stand providing arm/forearm support and relieving at least a portion of the weight of an arm and forearm of the patient with at least three degrees of freedom to simulate multi-joint coordination exercises that require coordination of the arm and hand, wherein the portion of the weight of the arm and forearm is relieved from the patient during the entire simulation of the multi-joint coordination exercises;

a plurality of arm/forearm movement sensors coupled to the exoskeleton for measuring arm and forearm movement and joint angles of the motor impaired stroke patient;

a sensor for measuring grasping force and release movement of the motor impaired stroke patient; and a computer controlled by virtual reality software and coupled to the arm/forearm movement sensors and sensor for measuring grasping force and release movement for generating a visual display of simulated multi-joint coordination exercises that require coordination of the arm and hand performed with enhanced motor ability relative to the actual impaired motor ability, wherein motivation of the patient to perform the upper-extremity rehabilitation movement therapy is provided by the computer automatically adjusting a plurality of parameters according to patient completion of the simulated multi-joint coordination exercises that require coordination of the arm and hand.

16. A computerized method for upper limb rehabilitation arm/forearm and grasping movement training of a patient comprising:

facilitating movement of an arm and forearm of the patient with a spring-actuated counterbalanced arm/forearm support which is an articulated exoskeleton worn by the patient and coupled to a stand relieving at least a portion of the weight of the arm and forearm of the patient;

relieving the portion of the weight of the arm and forearm from the patient during an entire simulation of multi-joint coordination exercises;

measuring impaired arm and forearm movements of the patient with at least three degrees of freedom in three dimensional space;

measuring impaired grasping force of the patient or impaired movement of a hand of the patient;

generating visual feedback to the patient of the simulated multi-joint coordination exercises that require coordination of the arm and hand in a virtual environment performed with enhanced motor ability relative to the actual impaired motor ability by use of a computer having arm/forearm measurement and grasping measurements as inputs; and motivating the patient to perform the upper limb rehabilitation movement training by the computer automatically adjusting a plurality of parameters according to patient completion of the simulated multi-joint coordination exercises that require coordination of the arm and hand.

17. The method of claim 16 where motivating the patient to perform the upper limb rehabilitation movement further comprises automatically varying the movement or range of motion required of the arm and forearm to successfully perform the simulated multi-joint coordination exercises that require coordination of the arm and hand based upon previous patient performance.

18. The method of claim 16 where motivating the patient to perform the upper limb rehabilitation movement further comprises automatically varying a threshold level required of the grasping force to successfully perform the simulated multi-joint coordination exercises that require coordination of the arm and hand based upon previous patient performance.

19. The method of claim 16 where facilitating movement of an arm and forearm of the patient with a spring-actuated counterbalanced arm/forearm support comprises employing an elastic suspension and a five degrees-of-freedom mechanism to counterbalances the weight of the arm and forearm using the elastic suspension.

20. The method of claim 16 where facilitating movement of an arm and forearm of the patient with a spring-actuated counterbalanced arm/forearm support comprises facilitating multi-joint coordination exercises that require coordination of the arm and hand reaching, drawing, eating, cooking, and cleaning movements in the virtual environment.

21. The method of claim 16 where facilitating movement of an arm and forearm of the patient with a spring-actuated counterbalanced arm/forearm support comprises employing a five degrees-of-freedom, back-drivable mechanism using elastic bands wrapped around two four bar linkages to counterbalance the arm/forearm.

22. The method of claim 16 where measuring impaired arm and forearm movements comprises measuring arm and forearm movements with a resolution of a distal tip of the spring-actuated counterbalanced arm/forearm support within 1 cm for each of a plurality of movement axes in the virtual environment.

23. The method of claim 16 where measuring impaired arm and forearm movements comprises measuring arm and forearm movements without initial zeroing, so that no initialization procedures are required.

24. The method of claim 16 where measuring impaired grasping force comprises measuring grasping force without initial zeroing, so that no initialization procedures are required.

25. The method of claim 16 where measuring impaired grasping force comprises measuring pressure changes in a fluidic bladder squeeze grasped by the patient.

26. The method of claim 16 further comprising communicating with a remote computer network coupled to the computer from which network and controlling the computer to set the parameters in a plurality of simulated multi-joint coordination exercises that require coordination of the arm and hand.

27. The method of claim 26 where controlling the computer to provide the parameters in a plurality of user-selected simulated multi-joint coordination exercises that require coordination of the arm and hand comprises setting the movement range and grasp threshold and target location for multi-joint coordination exercises that range the arm and forearm within the virtual environment.

28. The method of claim 16 further comprising generating quantitative feedback of performance.

29. The method of claim 16 further comprising generating a program of rehabilitative therapy and a corresponding therapeutic history of performance.

30. The method of claim 16 where facilitating movement of an arm and forearm comprises facilitating forearm and forearm supination and pronation, elbow flexion and extension, in combination with shoulder internal and external rotation, flexion and extension, and abduction and adduction.

31. A method for automating upper-extremity rehabilitation therapy for a motor impaired stroke patient comprising:

providing arm/forearm support using a spring-actuated counterbalanced gravity assistance exoskeleton worn by the patient and coupled to a stand relieving at least a portion of the weight of an arm and forearm of the patient;

relieving the portion of the weight of the arm and forearm from the patient during an entire simulation of multi-joint coordination exercises;

measuring arm and forearm movement of the motor impaired stroke patient with at least three degrees of freedom in three dimensional space;

measuring grasping force of the motor impaired stroke patient; and generating a visual display of the simulated multi-joint coordination exercises that require coordination of the arm and hand using a computer controlled by virtual reality software as if performed with enhanced motor ability relative to the actual impaired motor ability and having the measured arm/forearm movement and the measured grasping force or movement as inputs; and motivating the patient to perform the upper-extremity rehabilitation movement therapy by the computer automatically adjusting a plurality of parameters according to patient completion of the simulated multi-joint coordination exercises that require coordination of the arm and hand.

32. An apparatus for upper limb rehabilitation training of coordinated arm/forearm and grasping movements of a patient comprising:
- a spring-actuated counterbalanced arm/forearm support coupled to a stand relieving at least a portion of the weight of an arm and forearm of the patient and to facilitate movement of the arm and forearm of the patient wherein the portion of the weight of the arm and forearm is relieved from the patient during the entire simulation of the multi-joint coordination exercises;
- a arm/forearm measurement sensor capable of measuring impaired arm and/or forearm movements of the arm/forearm of the patient;
- a sensor capable of measuring impaired grasping force or impaired movement of a hand of the patient;
- a computer coupled to the arm/forearm measurement means and the grasping measurement means to process measurements of impaired arm/forearm and grasping movements to control a graphical representation of the arm/forearm and grasping force in interaction with a virtual environment, and to provide a visual feedback signal to the patient of the simulated multi-joint coordination exercises that require coordination of the arm and hand performed with enhanced motor ability relative to the actual impaired motor ability; and
- a display device coupled to the computer to display the visual feedback signal of the simulated multi-joint coordination exercises that require coordination of the arm and hand, wherein motivation of the patient to perform the upper limb rehabilitation movement training is provided despite limited motor ability.

* * * * *